United States Patent [19]

Spina, Jr. et al.

[11] Patent Number: 5,022,413

[45] Date of Patent: Jun. 11, 1991

[54] INTRALENTICULAR CATARACT SURGICAL PROCEDURE

[76] Inventors: Joseph Spina, Jr., 767 Woodlea Rd., Rosemont, Pa. 19109; Michael K. Weibel, 120 Gallows Hill Rd., West Redding, Conn. 06896

[21] Appl. No.: 184,333

[22] Filed: Apr. 21, 1988

[51] Int. Cl.$^5$ ............................................. A61B 19/00
[52] U.S. Cl. ...................................................... 128/898
[58] Field of Search .................. 604/893.1, 54, 20; 623/4–6; 128/897, 898; 523/111; 424/427, 428; 606/6

[56] References Cited

U.S. PATENT DOCUMENTS

| | | | |
|---|---|---|---|
| 2,114,370 | 4/1938 | Bickenheuser | 514/944 |
| 4,021,382 | 5/1977 | Stoy et al. | 623/4 |
| 4,078,564 | 3/1978 | Spina et al. | 604/51 |
| 4,135,516 | 1/1979 | Spina et al. | 128/303 R |
| 4,191,176 | 3/1980 | Spina et al. | 604/28 |
| 4,340,037 | 7/1982 | Lewicky | 604/28 |
| 4,365,050 | 12/1982 | Ivani | 523/106 |
| 4,386,927 | 6/1983 | Eichenbaum | 604/51 |
| 4,416,814 | 11/1983 | Battista | 623/11 |
| 4,452,600 | 6/1984 | Schachar | 604/51 |
| 4,452,776 | 6/1984 | Refojo | 623/4 |
| 4,554,156 | 11/1985 | Fischer et al. | 514/944 |
| 4,563,779 | 1/1986 | Kelman | 128/898 |
| 4,581,030 | 4/1986 | Bruns et al. | 623/4 |
| 4,584,188 | 4/1986 | Graham | 523/111 |
| 4,608,050 | 8/1986 | Wright et al. | 128/898 |
| 4,647,282 | 3/1987 | Fedorov et al. | 623/4 |
| 4,676,790 | 6/1987 | Kern | 128/898 |
| 4,787,885 | 11/1988 | Binder et al. | 604/294 |
| 4,795,436 | 1/1989 | Robinson | 514/955 |
| 4,819,617 | 4/1989 | Goldberg et al. | 128/897 |

OTHER PUBLICATIONS

Chambless, 11 Am. Intra-Ocular Implant Soc. J., 33–34 (1985).
Kessler, 7 Annals of Opthal., 1059–1062 (1975).
Bonnet et al., 69 Bulletin des Societes d'Ophtalmologi de France 596–612 (1969).
Schanzlin et al., *Cataract*, May 1985, pp. 11–14.

Primary Examiner—C. Fred Rosenbaum
Assistant Examiner—Sharon Rose
Attorney, Agent, or Firm—Dann, Dorfman, Herrell & Skillman; Dann, Dorfman, Herrell & Skillman

[57] ABSTRACT

Cataracts are treated for removal by introducing a lenticular tissue dispersing agent into the opacified lens through a small opening in the lens capsule so that the capsule remains substantially intact. The tissue dispersing agent is contained in the lens by a gel-forming substance which functions to block the opening in the lens capsule, preventing its escape. This treatment is preferably carried out in conjunction with laser induced phacofracture.

44 Claims, No Drawings

INTRALENTICULAR CATARACT SURGICAL PROCEDURE

BACKGROUND OF THE INVENTION

The present invention relates to the field of ophthalmic surgery, and in particular to intraocular procedures which facilitate cataract removal. Basically, the invention concerns treating the cataractous lens by introducing a lenticular tissue dispersing agent through a small opening in the lens capsule so that the lens capsule remains substantially intact. The tissue dispersing agent, which is preferably a hydrolytic enzyme capable of disrupting cellular adhesion in the lenticular tissue, is effectively contained in the lens by the use of a gel-forming substance which functions to block the opening in the lens capsule, preventing escape of the enzyme. Enzymatic dispersion of the lenticular tissue may be used to particular advantage in combination with a non-invasive technique for fragmenting the lens tissue, preferably, laser-induced phacofracture.

A cataractous eye is one in which an opacity develops that interferes with the normal transmission of light to the retina, thereby causing diminished vision. Although there are several types of fluids and tissues within the eye which may become opaque and cause a cataract, the vast majority of cataracts are associated with a clouding of the lenticular or lens tissue. These changes are irreversible and the only known remedy for the resultant blindness is surgical removal of the opaque lens tissue.

The lens of the eye is composed of several highly integrated structural components. The nucleus, which occupies about 60–75% of the lens volume, is composed of collapsed and layered cells which have lost virtually all intracellular organelles. The structure of the nucleus can be considered a lamellar assembly of membranes, comparable to the layers of an onion. Surrounding the nucleus is the cortex, which is generally soft and contains cells undergoing differentiation and elongation into nuclear cells. The exterior part of the cortex includes the highly proliferating epithelial cells contiguous to the lens capsule. Enveloping the lens itself, like an onion skin, is the transparent capsule, which is a structural protein complex whose composition is related to basal membrane collagen. Attached to the lateral, circular edge of the capsule and embedded within it are microscopic, suspensory tendrils called zonules. The zonules, in turn, are connected to the ciliary body of the eye which contains contractile tissue. Lens accommodation occurs by contraction or relaxation of the ciliary body. The resulting mechanical force is transmitted to the periphery of the lens capsule via the zonules. The radial tension at the capsule causes the ordinarily soft lens to flatten or upon reduction of tension to assume a more bulbous shape. Therefore conformational adaptation of the lens is the basis of refractive accommodation and hence the ability to focus on objects far or near.

For many years, the surgical procedure of choice for removal of cataracts was intracapsular extraction, in which the entire lens with its capsule is removed after disruption of the zonular attachment. An undesirable consequence of this procedure, however, is the removal of the physical partition separating the anterior segment aqueous fluid from the posterior segment vitreous fluid. Furthermore, the resulting aphakic (lensless) eye requires extraocular optical devices, such as thick eye glasses or contact lenses to compensate for loss of visual acuity.

More recently, the successful introduction of the intraocular lens (IOL) implant has substantially obviated postoperative optical correction and is now routinely practiced. The surgical procedure employed for cataractous lens removal in conjunction with IOL implants is known as extracapsular extraction. This procedure involves rupturing the anterior lens capsule, prolapsing the lens from the remaining capsular tissue into the anterior chamber and expressing it through a relatively large limbal incision. The primary difference between the intracapsular and extracapsular procedures is that in the latter, the posterior capsule is left intact. The posterior capsule maintains a natural barrier between the posterior and anterior segments of the eye, and together with the iris, physically supports the IOL within the lenticular region.

A requirement of the extracapsular procedure, is that the remaining capsular structure be carefully cleaned of adhering epithelial cells, which, if not removed, may later proliferate causing an opacity to develope, known as Elschnig's pearls. Although laser energy has reportedly been used to effect preoperative fracture of the opacified lens in cataract surgery, this phacofracture technique is not entirely satisfactory for extracapsular extractions. The laser-induced phacofracture technique described by Chambless, 11 Am. Intra-ocular Implant Soc. J. 33–34 (1985), for example, while effective in disrupting compact tissue, is relatively ineffective on softer cortical tissue. Cortical tissue is moderately elastic and difficult to mechanically disperse with the laser technique. Also, close proximity to the capsule precludes safe use of laser-induced phacofracture techniques on the cortex due to short range secondary effects of laser-induced cavitation which are largely uncontrollable. Therefore, the tissue fracture must be induced sufficiently interior to the capsular boundary to prevent cavitation damage to the lens capsule. For these reasons, the use of phacofracture alone has little practical effect on dispersion and removal of distal epithelial cells.

Even with the remarkable advances in the microsurgical techniques presently employed in intralenticular cataract surgery, the operation has been unable to yield an improved therapeutic result for the patient, in that removal of the opacified lens tissue results in loss of the adaptive focusing or accommodation of the eye. Presently, there is no post-operative prosthesis that can restore the accommodative function of the eye.

An accommodative lens prosthesis would require, by today's surgical procedure, reconstruction of the lens capsule and contents and reattachment to the zonular elements. Such reconstructive surgery is an impossible task with available or even contemplated technology. A conceptually simpler approach would be to leave the native lens capsule and related, contractile structures in place after surgical removal of the opaque tissue. Ideally removal would include nucleus, cortex and epithelial cells, the latter to prevent unorganized regrowth of lens tissue ultimately leading to opacification of the evacuated capsule. In order for this approach to succeed, a procedure must be provided for removing the highly integrated intracapsular tissue, yet maintaining the integrity of the capsule. Once thoroughly evacuated, the clear capsule could conceivably be refilled with a soft gel-like substance possessing an appropriate refractive index that could function like a native lens.

Evacuation of the lens tissue from within the lens capsule requires physical transfer of the contents across the capsular boundary. The most expedient and probably the most realistic approach would be to transform the intracapsular tissue into a liquid state which could be aspirated through a small diameter cannula penetrating the capsule. The more homogenous and fluid-like the contents become, the smaller the cannular dimension and the less trauma to the capsule. Likewise, in refilling the evacuated capsule, the smaller the hole in the capsule, the easier it will be to contain the injected fluid until in situ cross-linking or polymerization can occur to produce a flexible lens prosthesis.

Endocapsular removal of lens tissue and refilling of the evacuated capsule have been reported by Kessler, 7 Annals of Opthal. 1059-62 (1975), and more recently by Schanzlin et al., 12 Cataract, May, pp 11-14 (1985). Although the eye from which the lens was reportedly removed appeared to conditionally accommodate the prosthesis post-operatively, these procedures are generally unsatisfactory for practical application. It is questionable whether the micromechanical advancement in ophthalmic surgery alone will ever enable endocapsular removal of lens tissue in a manner which allows in situ reconstruction of an accommodative lens prosthesis. As noted above, what is needed is a procedure whereby the lens tissue within the capsule is fragmented, liquified or otherwise dispersed into a physical state allowing complete evacuation through a very small opening in the capsule.

Experimental in vitro softening of lens tissue employing proteolytic enzymes was reported as early as 1969 by Bonnet and Trouche, 69 Bulletin des Societes d' Ophtolmolgic de France 583-86 (1969). Subsequently Spina and Weibel developed a lenticular injection procedure which successfully contained injected lens digesting enzymes within the lens tissue, which is the subject of U.S. Pat. No. 4,078,564. Enzymatic dispersion of the lenticular tissue in this way is practicable because the lens capsule actually isolates the lens to such an extent that exogenous enzyme may be safely introduced into the lens without creating an immunologic foreign protein response thereto. This procedure was later refined for the removal of cataractous tissue in vivo by introducing highly specific tissue dispersing proteinases that reduce lens tissue to an aspiratible state, but do not digest the capsule. The latter procedure is the subject of U.S. Pat. No. 4,191,176, also granted to Spina and Weibel. It was believed that such a procedure would allow easier removal of lens tissue using atraumatic techniques such as simple aspiration in situ or after manipulation into the anterior chamber.

However, in experiments on senile cataracts, it has been found that this procedure is not satisfactory in penetrating hard nuclear tissue. These experiments have shown that injection of enzyme is largely confined to the cortex. The nucleus with its compact structure is dispersed by diffusion of the proteinase, achieving only slow, peripheral sloughing of nuclear cells. Due to inherent auto-inactivation mechanisms of the proteinase, the enzyme may be substantially deactivated before the nucleus is fully dispersed into an aspiratible state. A nucleus which is substantially reduced in size but remains a coherent tissue mass is not a problem in the conventional extracapsular procedure. The remaining lens is ultrasonically emulsified after prolapsing into the anterior chamber or simply expressed through the limbal incision. The presence of remaining coherent tissues, however, cannot be tolerated in endocapsular evacuation through a microcannula.

In order to effectively treat the sclerotic nuclear cataract it is important that the injected volume of the liquid dispersing agent be contained within the lens capsule and maintained in contact with the lenticular tissue. As previously mentioned, the tissue of the nucleus is not readily permeated by the treating agent and the injected fluid tends to form a fracture plane which ultimately produces a pocket within the tissue. This leads to a pocket of high, localized hydraulic pressure in the vicinity of the injection. Upon withdrawal of the microcannula the internal pressure is released by egress of the injected fluid back through the cannula track into the anterior chamber. It is important that the dispersive agent be retained within the lenticular region in order that it can act upon the target tissue. Furthermore, it is necessary to contain all of the injected agent in the lens to provide a consistent and predictable dose-related result.

In connection with our earlier enzymatic lens digestion procedure it was discovered that introduction of a small air bubble into the opening on the lens capsule through which the enzyme is delivered is an effective way of sealing the opening to prevent escape of the enzyme from the relatively soft lens of the test subject. This concept and related enzyme delivery devices are described in Spina and Weibel, U.S. Pat. No. 4,135,516, entitled "Delivery Apparatus and Method for Treatment of Intralenticular Cataracts With Exogenous Enzymes". This approach, however, has been found to be somewhat erratic in practice where the nuclear and cortical regions of the lens are extremely dense, or pressurized vaccuoles resulting from laser-induced cavitation are present. In general the pneumatic drive assembly which forces the contents of the microannula into the lens requires excessive volumetric compression for injection into the nucleus of the hard lens. Upon release of the dispersive agent, an uncontrolled surge of air into the injected lens can occur. This pneumatic surge may cause rupture of the lens capsule, escape of the delivered fluid about the cannula or other complications.

Against this background, it will be appreciated that an effective surgical procedure for completely removing the highly integrated cataractous tissue from the lens capsule, so as to allow refilling of the capsule with a material capable of restoring accommodative function of the eye, remains a highly desirable objective.

SUMMARY OF THE INVENTION

The difficulties experienced in earlier efforts to provide a practical and effective enzymatic cataract removal procedure have been substantially overcome by the enzymatic intralenticular cataract surgical procedure of this invention. According to one aspect of the invention, a tissue dispersive agent introduced into the lenticular tissue through a relatively small opening in the lens capsule can be effectively confined therein by sealing the opening with a gel-forming substance of relatively high viscosity. This may be conveniently accomplished in practice by using a delivery system for the tissue dispersive agent employing a hydraulic drive fluid which is viscosified with the gel-forming substance. For example, a suitably viscosified hydraulic drive fluid may be used in place of the pneumatic drive fluid in a delivery system of the type described in our U.S. Pat. No. 4,135,516. Delivery of the tissue dispersive agent in this manner is controllable, in that the relatively low viscosity enzyme solution in the cannula of the delivery system is gradually replaced by the higher viscosity gel-forming substance. This has the effect of increasing the pressure drop across of the delivery system as the cannula progressively empties, instead of decreasing the pressure, which results from the above-noted uncontrolled surge of gas that occurs when a pneumatic drive is used. Another advantage of using a hydraulically driven delivery system is that the drive fluid is not compressible, so that delivery of the tissue dispersive agent begins immediately upon activation of the delivery system.

According to another aspect of the invention, it has been found that our earlier enzymatic cataract removal procedure is surprisingly more effective when used in conjunction with laser-induced phacofracture. The combination of the two procedures avoids the limitations inherent in each one when utilized alone. The high efficiency of the laser-induced phacofracture technique in fragmenting the nucleus, combined with the high efficacy of the enzymatic procedure in dispersing the fragmented nuclear material, cortical and epithelial lens tissue now makes possible the simple, atraumatic evacuation of lens tissue from within the lens capsule.

Thus, the procedure of the present invention enables the safe removal of cataractous lenses while leaving the lens capsule intact and in condition for refilling with a substance capable of forming an accommodative prosthesis.

DETAILED DESCRIPTION OF THE INVENTION

The use of exogenous enzymes as tissue dispersive agents in intralenticular cataract surgery is generally described in our U.S. Pat. Nos. 4,078,564 and 4,191,176, the entire disclosure of each of which is incorporated by reference in the present specification as if set forth herein in full. Our prior procedure accomplishes extracapsular extraction by injection of an enzyme solution and aspiration of the dispersed lenticular tissue through a relatively small opening in the lens capsule. The present invention represents an improvement in our prior procedure, which is achieved by means of a gel-forming substance that seals the enzyme within the lens capsule by capillary blockage of the injection opening, thereby ensuring containment of the entire dosage unit to provide a consistent and predictable dose-related response in the treatment of cataracts.

Various water-soluble, high molecular weight natural or synthetic polymers can serve as the gel-forming substance that seals the opening in the lenticular tissue against egress of the tissue dispersive agent. Representative natural polymers which may be used in the practice of the invention include modified forms of cellulose, e.g. cellulose ethers, cross-linked guar, hydrolytically-modified and substituted starches, microbial extracellular polymers such as xanthan gum or glucoschlerans, plant exudates, such as gum tragacanth, plant extracts, such as pectin, pectin derivatives, carrageenan or other hemicelluloses, or tissue isolates such as alginic acid, haluronic acid, or collagen.

A wide variety of water-soluble synthetic polymers may also be used, if desired, such as polyvinyl alcohol, polyvinyl or styrene sulfonates, polyacrylates, polyacrylamides, polyvinyl pyrollidone, polyethylene glycol, and the like. Suitable polymers are those which are acceptable for injection into human tissue (biopolymers), and which do not interfere with the action of the tissue dispersive agent.

Particularly preferred are gel-forming substances that exhibit thixotropy and pseudoplastic behavior. The selection of thixotropic/pseudoplastic gel-forming polymers for the practice of this invention is important for two reasons. First, pseudoplastic polymers exhibit shear thinning, which is desirable because the viscosity of the polymer will decrease under shear as it is forced through the thin cannula. Second, thixotropic polymers develop progressive, time-dependant gel strength or elastic modulus. Accordingly, after flow stops, these polymers develop gel structure, which enhances capillary blockage and is important for preventing loss of injected fluid back through the cannula track. The elastic modulus of the gel-forming substance is preferably at least 100 Newtons/meter$^2$, developed within a few seconds. The gel-forming substances are normally employed at a relatively low concentration on the order of 0.1 to 5% by weight (w/w).

Although high molecular weight natural polymers are preferred as the gel-forming substance, high concentrations, up to 70% w/w, of low molecular weight, biologhcally compatible substances, such as glucose, may also be used, if desired, to enhance viscollastic properties.

The lenticular tissue dispersive agent may be delivered to the cataract by means of any reliable injection device, such as a manual syringe. A preferred device for delivery of the tissue dispersive agent is described in our U.S. Pat. No. 4,135,516, the entire disclosure of which is also incorporated by reference in the present specification, as if set forth herein in full. This delivery system comprises three principal parts, namely, a precision liquid dispensing unit capable of delivering the desired dosage unit of tissue dispersive agent required for operating on a lens, a distribution valve, and a microcannula. The assembly and operation of this device as a pneumatic system is described in detail in our foresaid U.S. Pat. No. 4,135,516. The system may be readily adapted for hydraulic operation by those skilled in the art, the drive fluid being viscosified with the gel-forming substance. The entire delivery system may be presterilized, e.g. by pasteurization, or conveniently cold sterilized by chemical means, and then rinsed with a sterile solution. Thereafter, the enzyme solution is rapidly loaded into the assembly, preferably within several minutes after preparation. When competently handled, this system will reliably and reproducibly deliver a predetermined volume of enzyme solution into the lens with virtually no leakage into the anterior chamber.

Laser-induced phacofracture, which is used to promote initial fragmentation of the lenticular tissue, according to the present invention, is generally described in Chambless, Am. Intra-ocular Implant Soc. J., supra. Appropriate power levels and numbers of pulses will generally vary, based on the degree of nuclear sclerosis, and may be determined empirically. Best results are obtained when laser-induced phacofracture is performed prior to injection of the tissue dispersive agent. The order of these two steps may be reversed, however, without adversely affecting the procedure. Other operating techniques and surgical equipment required for surgery on the lens itself are well known to experienced ophthalmologists, and, as they constitute no part of this invention, will not be described in detail herein.

The viscosified hydraulic drive fluid used for delivering the tissue dispersive agent to the cataractous lens and sealing the same therein preferably includes a tracking dye, such as fluorescein, or an alkali metal salt thereof, methylene blue, or dichloroindophenol, at a concentration from about 0.01 to about 1% w/v. The tracking dye indicates and enables observation of the distribution pattern of the tissue dispersive agent within the lens. The dye-containing hydraulic drive fluid is easily prepared by mixing solutions of appropriate concentration in a suitable mixing device. Mixing of the gel-forming substance and the tracking dye is conveniently carried out in the barrel of a sterile syringe. The resulting drive solution is sterilized by pasteurization before use.

A solution of cataractous tissue dispersive agent is prepared from a high purity enzyme by the addition of an appropriate volume of a physiologically acceptable medium, such as balanced salt solution (BSS). The enzyme solution is chilled until use, which preferably is no longer than four hours after preparation. The dispersion of cataractous tissue in situ requires high levels of enzyme activity and selectivity. Several classes of highly active exogenous enzymes are known to disperse selectively tissue components similar to those found in the human lens. These are proteases, lipases and carbohydrases, which respectively promote hydrolysis of proteins, lipids and various carbohydrates, including polysaccharides, which influence cell-cell adhesion. With high purity forms of enzymes, such as crystaline enzymes, concentrated solutions of up to 10% w/w may be formulated in a physiologically acceptable medium, such as buffered saline. Good results have been obtained using a concentrated crystalline trypsin solution, especially bovine or porcine trypsin, as the tissue dispersive agent. Mixtures of two or more enzymes, for example, a protease and a lipase may be used for best results.

An average human lens can accommodate up to twenty microliters of liquid without increasing the intraocular pressure so much that rupture of the lens capsule occurs. Thus by using a concentrated enzyme solution (10% w/w), as much as two milligrams of pure enzyme may be introduced into the lens without causing excessive pressure. Since a normal lens weighs about two hundred milligrams, an enzyme to substrate ratio of about 1:100 is readily obtainable. This constitutes a high enzyme:substrate ratio, particularly since the layered nature of the lens tissue places virtually all of the lens cells into essentially direct contact with the enzyme solution.

While the concentration of the enzyme solution may range from about 0.1% to about 10% w/w, the more concentrated the solution, the better. The optimum concentration for a particular enzyme may be determined empirically. If the enzyme concentration is insufficiently high, digestion of the lens substance requires more time, and mechanical removal of the lens residue may be necessary. On the other hand, the more concentrated enzyme solution will digest the lens more rapidly and to a greater degree. Due to the isolating effect of the lens capsule, high enzyme concentrations should not cause adverse results. The composition of the tissue dispersive agent and the intralenticular incubation time may be adjusted to achieve a high level of dispersion of the lens tissue.

Termination of the dispersion process and protection of other intraocular structure, in the event of escape of the tissue dispersive agent from the lens capsule, can be achieved by introduction of specific enzyme inhibitors into the anterior chamber of the eye. Enzyme inhibitors may be routinely used as a precaution against such leakage. High molecular weight inhibitors will not permeate the lens capsule and therefore will not interfere with dispersion of the lens tissue. Low molecular weight inhibitors may diffuse through the lens capsule and therefore are useful to terminate enzymatic dispersion external and internal to the lens itself.

The tissue dispersive agent is gradually deactivated and within a few days the cataractous lens tissue should be dispersed sufficiently for irrigation and aspiration.

One exemplary mode of practicing the present invention involves preoperatively fragmenting the lens by subjecting it to laser energy, followed by the introduction of a concentrated solution of exogenous enzyme into the lens capsule. This may be readily accomplished by injection through a microcannula at the sclera or at the scleral-corneal juncture of the eye. Thereafter, the opening in the capsule is sealed by the gel-forming substance and sufficient time is allowed for enzymatic dispersion of the lens to occur. Subsequently, the dispersed lens tissue is removed by conventional aspiration and irrigation techniques, employing, for example, the techniques described in the medical literature for removing congenital or soft cataracts. Desirably, the dispersed lenticular tissue is aspirated through the original microcannula track.

The following examples are provided to describe the improved intralenticular cataract surgical procedure of the invention in further detail. These examples, which are intended to illustrate and not to limit the invention, set forth the best mode presently contemplated for practicing the invention.

The surgical procedures described in the examples were performed on New Zealand white rabbits ranging in weight from 3 to 5 pounds. The test animals were anesthetized by intramuscular injection of 1 ml. of the combination of Ketemin TM and Rompum TM at a ratio of 7:1. The animals were maintained in an anesthetized state by periodic supplements of 0.2 ml. of the anesthetic administrated intramuscularly. The eyes were dilated using 1% Mydriacyl (tropicamide), 1% Isopto Atropine Sulfate TM and 10% viscous Neosynephrine TM (phenylephrine hydrochloride).

Trypsin was used as the tissue dispersive agent in the following examples. Sterile vials of high purity trypsin were obtained from Sigma Chemical Company and the injection solutions prepared as needed by addition of the appropriate volume of balanced salt solution into the vial. The solutions were stored on ice until used. In no case were trypsin solutions employed more than four hours after their preparation. Sterile technique was employed for transfer of trypsin from the makeup vial into the 100 microliter gas-tight glass syringe used to load the calibrated microcannula within the enzyme delivery system. The enzyme injection with the microcannula was conducted through a small Ziegler knife incision in the limbus.

Laser-induced phacofracture was performed using a YAG laser (yttrium-aluminum-garnet; Q-switched) model 9900, manufactured by Coherent. Power levels and numbers of pulses were as indicated in the examples below for each animal.

In each of the experimental procedures described in the examples, endocapsular aspiration for the majority of the test animals was conducted with a Cavitron 9001 irrigation-aspiration unit employing a 0.5 mm. tip, unless otherwise indicated. Aspiration was conducted through a vertical slit in the anterior capsule comprising 75% of the apparent diameter of the lens. Capsular perforation was performed using standard cystitome technique. The irrigation solution employed was a glucose and glutathione-fortified BSS solution containing 5 mls. of 1% heparin and 0.5 mls. of 1% epinepherine per liter. Post-operatively, the eyes of the test animals were salved with an antibiotic ointment and atropine ointment.

EXAMPLE I

Preparation Of Hydraulic Drive Fluid Viscosified With High Molecular Weight Polymers A hydraulic drive fluid, containing 1% w/v haluronic acid and 0.1% w/v fluorescein was prepared by introducing 44 microliters of a 1% w/v fluorescein solution into a sterile syringe barrel containing 0.4 ml. of 1.0% w/v Healon TM (a commercial form of haluronic acid) solution using sterile technique. The two solutions were mixed within the barrel of the syringe by longitudinal and rotary movement of the plunger. Aliquots of the mixture were directly transferred, using aseptic technique, to a sterile gas-type 50 microliter drive syringe within the hydraulically operated enzyme delivery system and used in the test procedures described below.

Two other viscosified hydraulic drive fluids were similarly prepared. One was a 2% w/v solution of the plant extract carrageenan; the other was a 1% solution of the microbial extracellular polymer xanthan gum.

EXAMPLE II

Enzyme Injection With Viscosified Hydraulic Drive Fluid

Three rabbits, closely matched in size, received enzyme injections using one of the three different hydraulic drive solutions prepared as described in Example I above. The enzyme concentration employed was 10 mg/ml trypsin in BSS containing 0.1% w/v fluorescein. The animals were labeled A (1% w/v haluronic acid), B (1% w/v xanthan gum) and C (2% w/v carregeenan). Each animal received two injections, consisting of 2.4 µl enzyme and 3 to 5 µl of the viscosified drive fluid, of which at least one 2.4 µl portion was injected into the cannula track as the cannula was withdrawn to seal the capillary-sized channel. One injection was placed superiorly in the cortex and the other approximately 120° to 180° inferiorly, also in the cortex. The enzyme was well contained within the lens in all cases as judged by slit lamp examination with the operating microscope. The right eye of each test animal received no treatment and served as a control.

A fourth animal, labeled D, received twice the enzyme dose, consisting of two injections of 20 mg/ml trypsin in BSS containing 0.1% w/v fluorescein, employing the 1.0% w/v xanthan gum hydraulic drive The injected eye of animal D was subjected to aspiration on after 24 hours and the lens was found not to be aspiratible in the nuclear region. Of the remaining three test animals, A-C, the lens in each injected eye was found to be completely aspiratible after 48 hours. The control lenses were partially aspiratible in the cortical region, but were not aspiratible in the nuclear region. Typically, a 5 to 7 mm diameter spherical nuclear core remained which was expressed through an enlarged limbal incision. The results of this test are set forth in Table I.

TABLE I

| Test Animal | | Enzyme Dose | Hydraulic Drive Fluid | Incubation Time | Lens Aspiration |
|---|---|---|---|---|---|
| A | OS | 2 × 2.4 ul 10 mg/ml | 1% haluronic acid | 48 hrs. | nucleus aspiratible |
|   | OD | None | — | — | nucleus not aspiratible |
| B | OS | 2 × 2.4 ul 10 mg/ml | 1% xanthan gum | 48 hrs. | nucleus aspiratible |
|   | OD | None | — | — | nucleus not aspiratible |
| C | OS | 2 × 2.4 ul 10 mg/ml | 2% carageenan gum | 48 hrs. | nucleus aspiratible |
|   | OD | None | — | — | — |
| D | OS | 2 × 2.4 ul 20 mg/ml | 1% xanthan gum | 24 hrs. | nucleus not aspiratible |
|   | OD | None | — | — | nucleus not aspiratible |

The tests results set forth in Table I indicate that capillary blockage of the cannula may be achieved with a viscous hydraulic drive fluid, thereby confining the injected enzyme dose within the lens. The lenses injected in this fashion are fully aspiratible after 48 hours In a comparative test, the nucleus was not fully aspiratible after 24 hours, although twice the enzyme dose was employed, indicating that a minimum time is required for the enzymatic softening and dispersion of the lenticular tissue.

EXAMPLE III

Enhancement of Enzyme Activity On Lens Tissue Using Laser-Induced Phacofracture

Two other rabbits, labelled E and F, were selected to undergo the following test procedure. Test animal E received relatively high laser energy consisting of 190 laser pulses at 9 millijoules in the left eye and two injections of 2.4 µl of a trypsin solution, at a concentration of 10 mg/ml, directly into the nuclear region of the lens. The viscous hydraulic drive fluid was 1.0% w/v xanthan gum in BSS containing 0.1% w/v flourescein, and approximately 5 µl of the drive fluid was used to seal the cannula track. The right eye of test animal E received no treatment and served as a control.

Test animal F received a substantially lower laser energy level consisting of 110 pulses at 5.9 millijoules in the left eye and enzyme treatment equivalent to that recorded for test animal E. The right eye of test animal F served as the laser treatment control and received 112 pulses at 5.9 millijoules with no enzyme injection.

The lenses of both test animals were aspirated after 24 hours. It was found that the lens nucleus left eye of test animal E which was subjected to combined high laser energy and enzyme treatment was completely aspiratible. The right eye, receiving no treatment, was not aspiratible at the highest power level of the equipment. A nucleus approximately 5 mm remained, which was expressed through an enlarged limbal incision.

The lens of the left eye of test animal F, which received combined low laser power and equivalent enzyme treatment to animal E, was not completely aspiratible. The size of the resultant nuclear mass was reduced as compared with the control, and measured approximately 3-4 mm. This nuclear mass required expression from the eye through an enlarged limbal incision. The right eye of test animal F, which received only laser treatment at a relatively low level, was not aspiratible and the nucleus was similar in size and consistency to the control of test animal E, which received no treatment. The expressed nucleus was approximately 5 mm in diameter. The results of the procedures performed on test animals E and F are set forth in Table II.

TABLE II

| Test Animal | | Enzyme Dose | Hydraulic Drive Fluid | Laser Treatment | Incubation Time | Lens Aspiration |
|---|---|---|---|---|---|---|
| E | OS | 2 × 2.4 ul 10 mg/ml | 1% xanthan gum | 192 pulses @ 9 millijoules | 24 hrs. | nucleus aspiratible |
|   | OD | None | — |  | 24 hrs. | nucleus not aspiratible 5 mm nucleus expressed |
| F | OS | 2 × 2.4 ul 10 mg/ml | 1% xanthan gum | 110 pulses @ 5.9 millijoules | 24 hrs. | nucleus not aspiratible 3 mm nucleus expressed |
|   | OD | None | — | 112 pulses @ 5.9 millijoules | 24 hrs. | nucleus not aspiratible 5 mm nucleus expressed |

These test results indicate that the laser treatment enhances the effect of the enzyme in softening and dispersing lens tissue. It should be noted that enzyme treatment alone, as in Example II, does not produce an aspiratible lens after 24 hours even with twice the normal enzyme dosage level. The effect of the laser treatment appears to be power dependent. Laser energy alone did not suffice to reduce the nucleus to a completely aspiratible state as was found in the laser control of test animal F. Only the combined high intensity laser and enzyme treatments produced a completely aspiratible lens within 24 hours under the test conditions. It is believed that the favorable effect produced by the laser-induced phacofacture procedure is a consequence of enhanced migration and intralenticular dispersion of the injected enzyme throughout the laser traumatized tissue mass thereby promoting disruption of cellular adhesion and subsequent tissue degradation.

While certain preferred embodiments of the present invention have been described and exemplified above, it is not intended to limit the invention to such embodiments, but various modifications may be made thereto, without departing from the scope and spirit of the present invention as set forth in the following claims.

What is claimed is:

1. In a method for treating the lens of an eye in vivo for the removal of lenticular tissue from the lens capsule containing said tissue by introducing within said lens capsule a lenticular tissue dispersing agent, allowing dispersion of said lenticular tissue to occur, and evacuating dispersed lenticular tissue from said lens capsule, the improvement which comprises treating said lenticular tissue by exposure to laser energy, thereby to promote disruption of cellular adhesion in, and dissemination of said dispersing agent through said lenticular tissue, said dispersing agent effecting dispersion of said laser-treated tissue.

2. A method as claimed in claim 1, wherein the steps of treating lenticular tissue by exposure to laser energy and introducing the dispersing agent are performed on cataractous tissue.

3. A method as claimed in claim 2 wherein the step of introducing dispersing agent is performed by injecting a biocompatible solution of at least one exogenous cataractous lens dispersing enzyme into the cataractous tissue through the lens capsule.

4. A method as claimed in claim 3 including the step of injecting hydrolytic enzyme selected from among a protease, a lipase, a carbohydrase or a mixture of one or more of said enzymes.

5. A method as claimed in claim 2 wherein the step of introducing dispersing agent is performed by injecting a biocompatible solution of trypsin into the cataractous tissue through the lens capsule.

6. A method as claimed in claim 2, wherein treating cataractous tissue by exposure to laser energy is performed in advance of introducing said dispersing agent.

7. A method as claimed in claim 2, wherein introducing said dispersing agent is carried out in advance of treating said tissue by exposure to laser energy.

8. A method as claimed in claim 2 wherein said dispersing agent is introduced within said lens capsule via hydraulic injection.

9. A method as claimed in claim 8 which includes the step of confining said dispersing agent within said lens capsule by blocking the injection opening with a gel-forming substance.

10. A method as claimed in claim 9 including the step of blocking said injection opening with a gel-forming substance selected from the group consisting of modified forms of cellulose, cross-linked guar, hydrolytically-modified and substituted starches, xanthan gum, glucoschlerans, gum tragacanth, pectin, pectin derivatives, carrageenan, alginic acid, haluronic acid and collagen.

11. A method as claimed in claim 2 including introducing said dispersing agent as a composition comprising a gel-forming substance.

12. A method as claimed in claim 2 wherein said dispersing agent is introduced as a composition comprising a tracking indicator.

13. A method as claimed in claim 2 wherein the dispersed lens tissue is evacuated from said lens capsule by aspiration.

14. A method for confining a treating fluid within the lens of an eye, comprising introducing said treating fluid into said lena through an opening therein and blocking said opening with at least one gel-forming substance.

15. A method as claimed in claim 2 including the step of blocking said opening with at least one gel-forming substance which exhibits thixotropy and is capable of developing an elastic modulus of at least about 100 Newtons/meter$^2$.

16. A method as claimed in claim 2 including the step of blocking said opening with a gel-forming substance selected from the group consisting of modified forms of cellulose, cross-linked guar, hydrolytically-modified and substituted starches, xanthan gum, glucoschlerans, gum tragacanth, pectin, pectin derivatives, carrageenan, alginic acid, haluronic acid and collagen.

17. A method as claimed in claim 14 wherein said treating fluid is introduced as a composition comprising a lenticular tissue dispersing agent.

18. A method as claimed in claim 14 wherein said treating fluid is introduced as a composition comprising a lenticular tissue dispersing agent and said gel-forming substance.

19. A method as claimed in claim 14 wherein said treating fluid is introduced as a composition comprising a lenticular tissue dispersing agent and a tracking indicator.

20. A method as claimed in claim 14 wherein said treating fluid is introduced as a composition comprising a lenticular tissue dispersing agent, a tracking indicator and said gel-forming substance.

21. A method as claimed in claim 20 wherein said treating fluid is introduced as a composition comprising from about 0.1% to about 10.0% w/w of an exogenous hydrolytic enzyme capable of disrupting cellular adhesion in the lenticular tissue, from about 0.1% to about 5% w/v of said gel-forming substance and from about 0.01% to about 1.0% w/v of said tracking indicator.

22. A method as claimed in claim 14 wherein said treating fluid is introduced into said lens through a conduit communicating with said opening, under pressure produced by a hydraulic medium.

23. A method as claimed in claim 22 wherein said treating fluid is introduced into said lens through a microcannula.

24. A method as claimed in claim 22 wherein said treating fluid is introduced into said lens through a conduit communicating with said opening, under pressure produced by a hydraulic medium comprising said gel-forming substance.

25. A method as claimed in claim 22 wherein said treating fluid is introduced as a composition comprising a lenticular tissue dispersing agent.

26. A method as claimed in claim 22 wherein said treating fluid is introduced as a composition comprising a hydrolytic enzyme capable of disrupting cellular adhesion in said lenticular tissue.

27. A method as claimed in claim 26 wherein said treating fluid is introduced as a composition comprising an enzyme selected from among a protease, a lipase, a carbohydrase or a mixture of one or more of said enzymes.

28. A method for confining a lenticular tissue dispersing enzyme within the lens of an eye comprising introducing said enzyme into said lens by hydraulic injection, using as the hydraulic medium a thixotropic gel-forming substance and blocking the injection opening with said gel-forming substance.

29. A method as claimed in claim 28 wherein the enzyme solution is introduced as a composition comprising at least one hydrolytic enzyme capable of disrupting cellular adhesion in said lenticular tissue and a thixotropic gel-forming substance selected from the group consisting of haluronic acid, carrageenan, xanthan gum, pectin and pectin derivatives.

30. A method as claimed in claim 28 wherein said enzyme solution is introduced as a composition comprising from about 0.1% to about 10% w/v of an enzyme selected from among a protease, a lipase or a carbohydrase and from about 0.1% to about 5% of gel-forming substance.

31. A method as claimed in claim 30 wherein the enzyme solution is introduced as a composition comprising trypsin and haluronic acid.

32. A method as claimed in claim 30 wherein the enzyme solution is introduced as a composition comprising trypsin and carrageenan.

33. A method as claimed in claim 30 wherein the enzyme solution is introduced as a composition comprising trypsin and xanthan gum.

34. A method as claimed in claim 28 wherein the enzyme solution is introduced as a composition including a tracking indicator.

35. A method as claimed in claim 34 wherein the enzyme solution is introduced as a composition comprising fluorescein or an alkali metal salt thereof as the tracking indicator.

36. A method for treating the lens of an eye in vivo for the removal of cataractous tissue from the lens capsule containing said tissue, which method comprises fragmenting said tissue by exposure to laser energy, introducing within said lens capsule via hydraulic injection a cataractous tissue dispersing agent, confining said dispersing agent within said lens capsule by blocking the injection opening with a gel-forming substance, allowing dispersion of said tissue to occur, and evacuating dispersed fragmented cataractous tissue from said lens capsule.

37. A method as claimed in claim 36 including the step of blocking said injection opening with a gel-forming substance selected from the group consisting of modified forms of cellulose, cross-linked guar, hydrolytically-modified and substituted starches, xanthan gum, glucoschlerans, gum tragacanth, pectin, pectin derivatives, carrageenan, alginic acid, haluronic acid and collagen.

38. A method for treating the lens of an eye in vivo for the removal of cataractous lens tissue from the lens capsule, while substantially maintaining the integrity of the lens capsule, which method comprises subjecting said lens tissue to non-invasive phacofracture, injecting into said lens tissue through said lens capsule a biocompatible solution of lens dispersing enzyme, confining said solution within said lens capsule by blocking the injection opening with a gel-forming substance, allowing said enzyme to effect dispersion of said cataractous lens tissue, and aspirating dispersed, cataractous lens tissue from said lens capsule.

39. A method as claimed in claim 38 wherein said biocompatible solution of lens dispersing enzyme comprises trypsin.

40. A method as claimed in claim 38 wherein said biocompatible solution of lens dispersing enzyme additionally comprises a tracking indicator.

41. A method as claimed in claim 38 wherein said biocompatible solution of lens dispersing enzyme comprises trypsin and fluorescein, or an alkali metal salt thereof.

42. A method as claimed in claim 38 wherein said non-invasive phacofracture is effected by exposing the lens tissue to laser energy consisting of from about 10 to about 200 laser pulses at from about 1 to about 20 millijoules, using a yttrium-aluminum-garret (YAG) laser.

43. A method as claimed in claim 38 wherein the step of confining said solution within said lens capsule is carried out by blocking the injection opening with xanthan gum.

44. A method as claimed in claim 38, wherein said gel forming substance is selected from the group consisting of haluronic acid, xanthan gum or carageenan.

* * * * *

UNITED STATES PATENT AND TRADEMARK OFFICE
CERTIFICATE OF CORRECTION

PATENT NO. : 5,022,413
DATED : June 11, 1991
INVENTOR(S) : Joseph Spina, Jr. and Michael K. Weibel It is certified that error appears in the above-indentified patent and that said Letters Patent is hereby corrected as shown below:

Column 2, line 29, change "11" to -- 11 --.
Column 3, line 17, change "7" to --7--.
Column 6, line 26, change "biolghcally" to --biologically--.
Column 9, line 48, change "Withdrawn" to --withdrawn--.
Column 9, line 61, delete --on--.
Column 10, line 53, after "lens nucleus" insert --of the--.

Signed and Sealed this

Twenty-fourth Day of August, 1993

Attest:

BRUCE LEHMAN

Attesting Officer

Commissioner of Patents and Trademarks